United States Patent
Boehm et al.

(10) Patent No.: US 10,206,767 B2
(45) Date of Patent: Feb. 19, 2019

(54) DENTAL PROSTHESIS FOR DETERMINING ABRASION FACETS

(71) Applicant: Heraeus Kulzer GmbH, Hanau (DE)

(72) Inventors: Uwe Boehm, Hanau (DE); Matthias Funk, Hanau (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 15/325,771

(22) PCT Filed: Jul. 13, 2015

(86) PCT No.: PCT/EP2015/065997
§ 371 (c)(1),
(2) Date: Jan. 12, 2017

(87) PCT Pub. No.: WO2016/008857
PCT Pub. Date: Jan. 21, 2016

(65) Prior Publication Data
US 2017/0151046 A1    Jun. 1, 2017

(30) Foreign Application Priority Data
Jul. 18, 2014  (DE) .................. 10 2014 110 154

(51) Int. Cl.
*A61C 13/08*  (2006.01)
*A61C 19/045*  (2006.01)
(Continued)

(52) U.S. Cl.
CPC ........ *A61C 19/045* (2013.01); *A61C 13/0001* (2013.01); *A61C 13/0003* (2013.01); *A61C 19/052* (2013.01); *A61C 13/0006* (2013.01)

(58) Field of Classification Search
CPC .............. A61C 19/075; A61C 13/0001; A61C 13/0003; A61C 19/052; A61C 19/045; A61C 13/0006
See application file for complete search history.

(56) References Cited

U.S. PATENT DOCUMENTS

| 4,396,377 A | 8/1983 | Roemer et al. |
| 5,270,350 A | 12/1993 | Muller et al. |

(Continued)

FOREIGN PATENT DOCUMENTS

| DE | 950958 C | 10/1956 |
| DE | 102009056752 A1 | 6/2011 |

(Continued)

OTHER PUBLICATIONS

Search Report in International Application No. PCT/EP2015/065997 dated Sep. 17, 2015, 6 pages.
(Continued)

*Primary Examiner* — Nicholas Lucchesi
(74) *Attorney, Agent, or Firm* — Marshall, Gerstein & Borun LLP

(57) ABSTRACT

The invention relates to a temporary dental prosthesis for determining abrasion facets, having at least one prosthetic tooth, in which at least the occlusion surface of the prosthetic tooth or at least one of the prosthetic teeth is made of a material that is abradable such that, within a maximum of 12 weeks of use as a dental prosthesis by a patient, abrasion facets are produced on the prosthetic teeth and are suitable for ascertaining the chewing movements of the jaw of the patient. The invention also relates to a method for determining the chewing movement of a set of teeth from measured abrasion facets, in which a temporary dental prosthesis made of an abradable material is inserted in a patient, and to a method for producing a final dental prosthesis.

9 Claims, 1 Drawing Sheet

(51) Int. Cl.
*A61C 13/107* (2006.01)
*A61C 19/05* (2006.01)
*A61C 13/00* (2006.01)

(56) References Cited

U.S. PATENT DOCUMENTS

| | | | |
|---|---|---|---|
| 5,458,489 A * | 10/1995 | Tennyson | A61C 13/26 |
| | | | 433/181 |
| 5,911,576 A | 6/1999 | Ulrich et al. | |
| 6,196,843 B1 * | 3/2001 | Kawaguchi | A61K 6/083 |
| | | | 433/212.1 |
| 6,843,654 B1 * | 1/2005 | Liu | A61K 6/083 |
| | | | 433/202.1 |
| 7,412,298 B2 | 8/2008 | Presswood et al. | |
| 8,506,299 B2 | 8/2013 | Gartner et al. | |
| 9,295,534 B2 | 3/2016 | Ruppert et al. | |
| 2001/0012861 A1 * | 8/2001 | Liu | C08F 255/02 |
| | | | 523/118 |
| 2004/0137409 A1 * | 7/2004 | Savic | A61C 13/0003 |
| | | | 433/203.1 |
| 2005/0059751 A1 * | 3/2005 | Erdrich | A61K 6/083 |
| | | | 523/113 |
| 2005/0112523 A1 | 5/2005 | Massad | |
| 2010/0297587 A1 * | 11/2010 | Zilberman | A61C 13/20 |
| | | | 433/223 |
| 2013/0073265 A1 | 3/2013 | Kraemer et al. | |
| 2013/0330689 A1 * | 12/2013 | Woldegergis | A61C 8/0001 |
| | | | 433/213 |
| 2017/0319306 A1 * | 11/2017 | Arnold | A61C 13/097 |

FOREIGN PATENT DOCUMENTS

| | | |
|---|---|---|
| EP | 497157 A2 | 8/1992 |
| EP | 1444965 A2 | 8/2004 |
| EP | 2570099 A2 | 3/2013 |
| JP | 2012-217622 A | 11/2012 |
| JP | 2013-512695 A | 4/2013 |
| WO | WO-91/07141 A1 | 5/1991 |
| WO | WO-2013/0123062 A1 | 8/2013 |
| WO | WO-2013/124452 A1 | 8/2013 |

OTHER PUBLICATIONS

Office Action in German Application No. 10 2014 110 154.5 dated May 6, 2015, 6 pages.
Office Action in EP Application No. 15 738 067.6 dated Sep. 5, 2018, 22 pages.
Office Action in JP Application No. 2017-502992 dated Sep. 12, 2018, 7 pages.

* cited by examiner

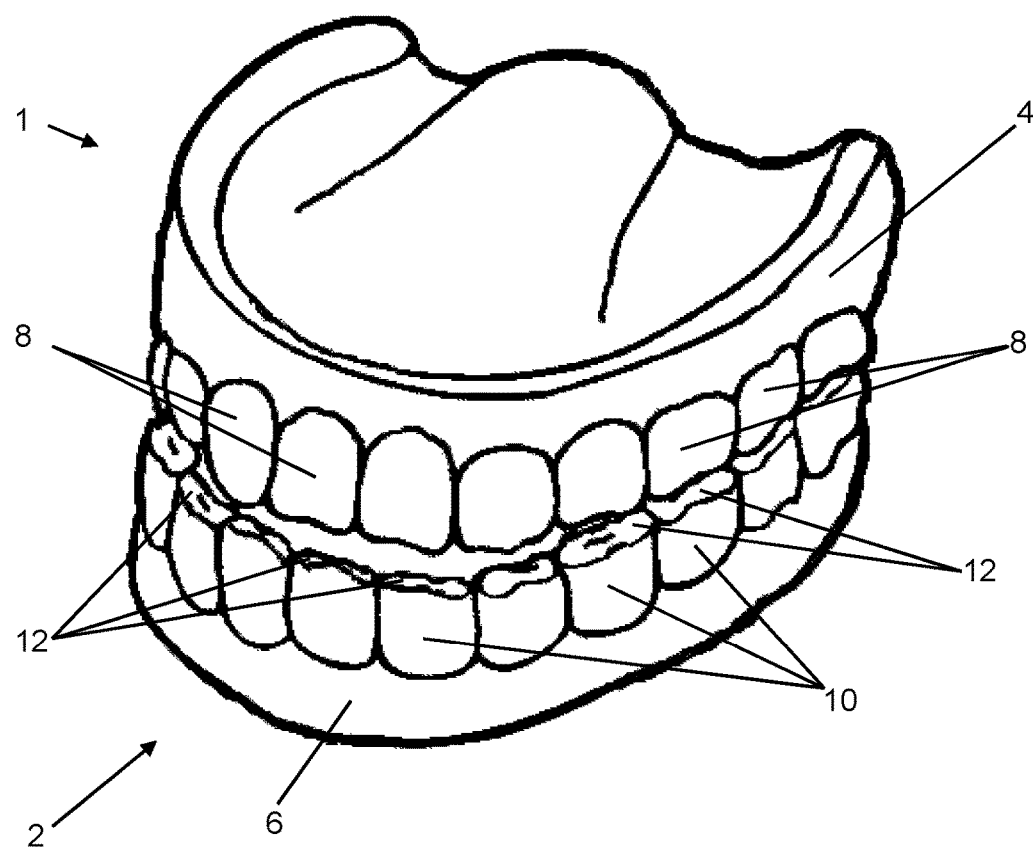

DENTAL PROSTHESIS FOR DETERMINING ABRASION FACETS

The invention relates to a temporary dental prosthesis for determining abrasion facets. The invention also relates to a method for determining the chewing movement of a dentition from measured abrasion facets and to a method for producing a final dental prosthesis.

The typical method used is analog creation of dental prostheses. In order to produce the prosthesis base, an analog method is thus usually used currently, in which an impression of the edentulous jaw of the patient is first taken. A mold is made from this impression, into which a gingiva-colored plastic material is poured. Once the plastic material has set, it is subject to secondary finishing in order to obtain the desired shape. The prosthetic teeth are then inserted into the mold and are connected to the prosthesis base during the casting process.

In order to produce the dental prosthesis, prosthetic teeth are fitted manually and individually on a wax base on a plaster model of the edentulous jaw. This wax prosthesis is embedded in the next step in a cuvette with plaster, silicone or gel (depending on the subsequent processing technique) so as to then wash out the wax base with hot water once the embedding material has set and create a cavity for the prosthesis plastic material. The prosthetic teeth remain here in the embedding material. A suitable plastic material is injected or poured into the cavity, such that the dental prosthesis is obtained once the plastic material has set. When fitting the prepared teeth, these are adapted and ground down by the dental technician and if necessary also by the dentist so as to suit the individual situation present in the oral cavity of the patient.

A method for producing a dental prosthesis is known from WO 91/07141 A1, wherein, in the case of that method, a prosthesis base based on an impression is milled from a block of synthetic material. There are already first methods, such as the methods known from DE 10 2009 056 752 A1 or WO 2013 124 452 A1, in which a partial or total dental prosthesis is constructed digitally and is produced via CAD-CAM methods. Optimized methods for producing dental prostheses using CAD-CAM methods are additionally known from EP 1 444 965 A2.

A disadvantage of the known methods is that the prosthetic teeth, when inserted in the prosthesis base, often have to be corrected again when fitted to the patient. To this end, the prosthetic teeth have to be either occlusally ground down or the prosthetic teeth are removed from the prosthesis base, basally ground, and then re-inserted. The occlusion function of the dental prosthesis is usually measured manually by inserting a thin colored sheet, on which the patient should then perform chewing movements when his/her jaw is closed. The areas of strong friction and high pressure on one another change color and are then ground away by the dentist. There are already more advanced methods here as well, in which the chewing movement is determined with the aid of articulators. Such methods have the disadvantage that they often can determine the natural chewing movement of the patient only incompletely. In addition, so as not to negatively influence the shape and the appearance of the prosthetic teeth, a certain effort has to be expended by the dentist in the case of occlusal grinding of the prosthetic teeth.

The object of the invention thus lies in overcoming the disadvantages of the prior art. In particular, a possibility is sought for determining the chewing movements of a patient where possible with normal use of a dental prosthesis so as to enable an improvement in the production of a final dental prosthesis. At the same time, a method applied here should be easily implemented to the greatest possible extent and preferably should be automated or capable of being automated. The determination of the jaw movement should be based where possible on the final dental prosthesis to be produced. At the same time, however, the method should not be too complex.

The objects of the invention are achieved by a temporary dental prosthesis for determining abrasion facets, having at least one prosthetic tooth, in which at least the occlusion surface of the prosthetic tooth or at least one of the prosthetic teeth is made of a material that is abradable such that, within a maximum of 12 weeks of use as a dental prosthesis by a patient, abrasion facets are produced on the prosthetic teeth and are suitable for ascertaining the chewing movements of the jaw of the patient.

When ascertaining or determining the chewing movement of the jaw of a patient, the abrasion facets are measured in respect of their position and depth, where appropriate also in respect of their shape, and the chewing function or the chewing movement of the jaw is recalculated from the data thus obtained.

Here, provision can be made such that a material thickness of at least 0.1 mm, in particular a material thickness of at least 0.5 mm, is eroded on at least one of the abrasion facets produced within a maximum of 12 weeks, wherein the abrasion facets are preferably produced by normal use of the dental prosthesis for a maximum of 12 weeks, particularly preferably a maximum of 4 weeks, very particularly preferably a maximum of 2 days.

It is thus ensured that the abrasion facets are thick enough to enable a sufficiently accurate ascertainment of the chewing movements on the basis of the measured abrasion facets.

In accordance with a particularly preferred embodiment of the present invention, provision can be made such that the abradable material is of such a nature that on a flat surface of the abradable material with two-media abrasion with respect to an aluminum oxide ball with a diameter of 4.75 mm under water, a volume loss of 0.01 $mm^3$ to 4 $mm^3$, preferably a volume loss of from 0.05 $mm^3$ to 3 $mm^3$, particularly preferably a volume loss of from 0.1 $mm^3$ to 2 $mm^3$ is created after 4,600 cycles, wherein with each cycle the aluminum oxide ball is placed on the surface, then rolled over the flat surface of the material over 0.8 mm with a force of 50 N, and then is lifted again from the surface.

This abrasiveness of the material is particularly well suited for the construction of temporary dental prostheses according to the invention, since the extent of the abrasion of the temporary dental prosthesis, with normal use of the temporary dental prosthesis by different patients, is suitable in order to utilize the abrasion facets produced during use of the temporary dental prosthesis in order to determine the chewing function of the jaw of the patient with sufficient quality. The quality of the abrasion facets is sufficient when the chewing function is determined so accurately that the final prosthesis produced with the chewing function data thus obtained can be so accurately adjusted in respect of the occlusion that the final prosthesis fits the patient, and there is preferably no longer any need for further secondary finishing of the occlusion surfaces by means of an adjustment performed by the dentist or a dental technician once the patient has been fitted with the final prosthesis. This can be checked in the conventional way, as is usual in the event of occlusal inspection by the dentist.

In this embodiment, provision can also be made such that the described volume losses as a result of two-media abrasion occur in a CS-4.2 or CS-4.4 chewing simulator from the company SD Mechatronik GmbH.

This construction is particularly well suited for standardizing the abrasion and therefore for standardizing and defining the properties of the abradable material.

Provision can also be made with a further development such that the temporary dental prosthesis is produced using a rapid prototyping method or by means of an abrasive method, preferably using fused layer modeling/manufacturing (FLM) of plastic or waxes, fused deposition modeling (FDM) of plastic or waxes, in particular of acrylonitrile-butadiene-styrene copolymer or polylactide, laminated object modeling (LOM) of plastic films, layer laminated manufacturing (LLM) of plastic films, electron beam melting (EBM) of plastic or waxes, multi jet modeling (MJM) of waxes or plastic, in particular of thermoplastic or UV-sensitive photopolymers, polyamide casting of polyamides, selective laser melting (SLM) of plastic, selective laser sintering (SLS) of plastic or waxes, in particular of thermoplastic such as polycarbonates, polyamides or polyvinyl chloride, 3D printing (3DP) of plastic granulate, or plastic powder, space puzzle molding (SPM) of plastic or waxes, stereolithography (STL or SLA) of plastic or waxes, grinding or multi-axis milling methods, in particular of a liquid resin, thermoset or elastomer, or digital light processing (DLP) of photopolymerisable liquid plastic.

With these methods, the temporary dental prostheses can be made easily and in a fully automated manner. In particular with use of modern CAD-CAM methods, the data already required can also be used easily for the manufacture of the temporary dental prosthesis.

For use on the patient it is necessary that the abradable material is biocompatible.

It is thus ensured that the particles produced during the abrasion are not harmful to the patient.

Provision can be made such that the occlusion surface or the occlusion surfaces, the coronal end or the coronal ends, the prosthetic teeth or rows of prosthetic teeth, the maxillary dental prosthesis, or mandibular dental prosthesis, or the total temporary dental prosthesis are made of the abradable material.

The term "coronal" (lat. corona ('crown')) means at the crown of a tooth and towards the crown of a tooth when designating a position and direction at the teeth, comprising the occlusal surface and the peripheral areas of the teeth or prosthetic teeth surrounding the occlusal surface.

These parts are sufficient for the implementation of a method according to the invention, in which the chewing function of the jaw of the patient is determined deliberately with the aid of the temporary dental prosthesis. In order to enable a comfortable fit of the temporary dental prosthesis, it can be advantageous when the prosthesis base of the temporary dental prosthesis is made of a material other than the abradable material. A particularly economical temporary dental prosthesis is obtained when the entire temporary dental prosthesis is made of the abradable material.

In accordance with a particularly preferred further development of the invention, it is proposed that the occlusion surfaces of the prosthetic teeth arranged in occlusion each consist of the abradable material paired with another material more resistant to abrasion, wherein in particular the material more resistant to abrasion is harder than the first material, wherein the prosthetic teeth of the maxilla or the prosthetic teeth of the mandibular preferably are made from the abradable material.

The abrasion facets can thus be produced selectively on specific prosthetic teeth, for example on the occlusion surfaces of the prosthetic teeth of the maxilla or mandibular. This is particularly advantageous for determining the chewing movement, since a mutual influencing of the abrasion facets produced during use of the temporary dental prosthesis thus can be ruled out and therefore no longer has to be taken into consideration when determining the chewing movement.

Provision can also be made in accordance with the invention such that the abradable material comprises a plexiglass, a non-cross-linked polymethylmethacrylate, and/or an unfilled, non-cross-linked thermoplastic, and the abradable material preferably is a plexiglass, a non-cross-linked polymethylmethacrylate, or an unfilled, non-cross-linked thermoplastic.

These materials can be produced effectively with the desired physical properties, such that the desired abrasiveness is provided. As a result of a reduced cross-linking, the structural cohesion of the material is weakened in such a way that particles can be removed from the material more easily under mechanical loading, thus resulting in an increased rate of erosion.

The objects forming the basis of the invention are also achieved by a method for determining the chewing movement of a dentition from measured abrasion facets, in which a temporary dental prosthesis made of an abradable material, preferably a dental prosthesis according to the invention, is inserted in a patient, and after a maximum of 12 weeks of use of the temporary dental prosthesis, preferably after a maximum of 4 weeks of use of the temporary dental prosthesis, the abrasion facets on the dental prosthesis are measured and the chewing movements of the dentition of the patient are calculated from the measured abrasion facets.

The chewing movements are preferably ascertained dynamically.

In such methods provision can be made such that the temporary dental prosthesis is produced by means of an RP method or by means of an abrasive method.

Provision can also be made such that the centric occlusion is determined prior to the production of the temporary dental prosthesis.

When determining the centric occlusion of a jaw, the position of the maxilla and of the mandibular relative to one another with teeth and/or a suitable dental prosthesis in a pressed together (clenched) state of the jaw is determined for the patient.

It is thus possible to ensure that the produced temporary dental prosthesis is made to such a good basic standard in respect of the occlusion that the abrasion facets are not influenced by a chewing movement distorted by an imperfect occlusion of the jaw.

With a preferred further development of the method according to the invention, it is also proposed that the abrasion facets of the used temporary dental prosthesis are measured using a scanner, the position, depth and/or shape of the abrasion facets is determined using a computer, preferably by means of a comparison of a recording of the unused temporary dental prosthesis, or of a CAD model of the unused temporary dental prosthesis forming the basis for production of the temporary dental prosthesis, with the used temporary dental prosthesis, and the chewing movement of the jaw is calculated from the data, thus obtained, relating to the abrasion facets. The abrasion facets can be ascertained by an intra-oral recording or the recording of the dental model or the used temporary dental prosthesis by means of tabletop scanners.

The method can thus be automated, such that the entire method can be carried out with the aid of a suitable computer program.

The objects forming the basis of the invention are lastly also solved by a method for producing a final dental prosthesis in which a method as described above for determining the chewing movement of a jaw from abrasion facets is applied and in which the position and orientation of the prosthetic teeth of the final dental prosthesis is calculated on the basis of the data relating to the chewing movements of the jaw of the patient ascertained using the temporary dental prosthesis, and the final dental prosthesis is produced on the basis of this calculation, in particular using a CAD-CAM method.

The invention is based on the surprising finding that it is possible, by use of an easily abraded or an abradable temporary dental prosthesis, for abrasion facets to be produced in the temporary dental prosthesis over a short period of time with the natural movements of the jaw or with normal use by the patient, which abrasion facets are suitable for determining or for ascertaining the natural chewing movements of the jaw of the patient. Very good conclusions regarding the chewing movements of the jaw can then be drawn from the position, depth and shape of the abrasion facets and are suitable for optimising the construction of the final dental prosthesis. The invention provides a method and a material for producing functionally optimized temporary dental prostheses.

The concept forming the basis of the present invention can be considered the fact that, once the centric occlusion has been determined using known methods, an economical temporary dental prosthesis is created in the conventional way or by means of RP methods or by means of abrasive methods (such as automatic grinding or milling). The used materials are biocompatible. At least in the case of part of the temporary dental prosthesis, i.e. in the case of the temporary dental prosthesis for the maxilla or the mandibular, the artificial prosthetic teeth or at least the occlusal surfaces thereof are produced from a very abradable material, such that abrasion facets are formed after a short period of wearing the prosthesis (preferably hours to days). The temporary dental prosthesis thus produced serves exclusively to construct the functionally optimal prosthetic teeth as quickly as possible from the chewing movement in the case of an edentulous jaw.

The abrasion measured subsequently is analyzed for example using suitable software. As a result, it should be possible to design a functionally optimized dental prosthesis and to realize or produce this as a final dental prosthesis using known methods.

In order to be able to determine the abrasiveness of the material to be used and thus establish the suitability of the abradable material for a temporary dental prosthesis according to the invention, a two-media abrasion (a chewing simulation) can be carried out by way of example and preferably in accordance with the invention. Such a method proceeds for example as follows:

The test specimen is produced from the desired or considered abradable material and the antagonists are produced or provided (aluminum oxide balls, 4.75 mm diameter) in prefabricated REM carriers (9 mm diameter)

The test specimen is polymerized in accordance with the manufacturer's instructions The samples are first ground wet using no. 1000 and then no. 4000 SiC paper The samples are then subjected to alternating thermal loading by applying the following cycles, which are each repeated 5000 times:
1. 30 seconds immersion in cold water at 5° C.;
2. 10 seconds allowed to drain;
3. 30 seconds immersion in warm water at 55° C.; and
4. 10 seconds allowed to drain.

Once the thermal loading is complete or after 5000 cycles for thermal loading, the test specimens and the antagonists are placed in a chewing simulator (the test specimens are constantly under water). During the actual abrasion procedure, the following cycles are carried out 4,600 times:
1. the antagonists are placed against the sample with a force of 50 N;
2. the sample is moved horizontally under this load by 0.8 mm; and
3. the antagonists are lifted from the sample.

As a result of this course of movement, a clearly visible round to slightly oval recess is formed on the sample.

The results or the abrasion recesses can be analyzed for example as follows:

The recesses produced are analyzed using a contactless surface laser scanner (Microfocus system).

An area of 2.5 mm by 2.5 mm (depending on the size of impression also 3 by 3 mm$^2$) is measured. Here, it should be noted that the recess to be measured is central in relation to the total measurement area (the edge around the recess may be used or required by software for orientation of the test specimen).

The laser ascertains the surface nature of the abraded area or recess. Here, the maximum depth of each recess is determined in μm, and the volume loss is determined in mm$^3$.

By way of example, a CS-4.2 or a CS-4.4 apparatus from the company SD Mechatronik GmbH (previously: Willytec GmbH) can be used as chewing simulator.

Here, the following parameters can be used as test parameters: stroke height 5.0 mm, stroke depth 0.8 mm, lowering speed 20 mm/s, lifting speed 50 mm/s, forward speed 30 mm/s, backward speed 50 mm/s, loading of the sample 50 N. $Al_2O_3$ balls having a diameter of 4.75 mm can be used as antagonists.

A suitable surface scanner can be obtained from the company OPM GmbH. The following can be selected as measurement parameters: measurement area 2.5×2.5 mm$^2$ (3×3 mm$^2$ as necessary), resolution 100 pixels/mm and z-axis resolution 0.1 μm.

Further exemplary embodiments of the invention will be explained hereinafter on the basis of a schematically illustrated drawing, without limiting the invention hereto. FIG. 1 shows a schematic illustration of a temporary dental prosthesis according to the invention.

The illustrated temporary dental prosthesis is a two-part total prosthesis which is used as an aid for producing a final dental prosthesis to be fitted in a completely edentulous jaw. The two-part dental prosthesis consists of a maxillary dental prosthesis 1 and a mandibular dental prosthesis 2. The maxillary dental prosthesis 1 has a prosthesis base 4. The mandibular dental prosthesis 2 also has a prosthesis base 6.

The prosthesis bases 4, 6 rest in the patient on the edentulous jaw ridge. A row of prosthetic teeth 8 for the maxilla and a row of prosthetic teeth 10 for the mandibular are arranged in the prosthesis bases 4, 6 respectively. The row of prosthetic teeth 8 of the maxilla forms an occlusion plane with the prosthetic teeth 10 of the mandibular. The appropriate occlusion plane was determined using known methods for determining the centric occlusion.

In the perspective view according to FIG. 1, only occlusion surfaces 12 of the prosthetic teeth 10 of the mandibular dental prosthesis 6 can be seen. The prosthetic teeth 8 of the maxillary dental prosthesis 4 have corresponding occlusion surfaces, however these are not visible in FIG. 1 on account of the perspective. The occlusion surfaces of the prosthetic teeth 8 of the maxillary dental prosthesis 4 bear in the pressed together (clenched) state against the occlusion surfaces 12 of the prosthetic teeth 10 of the mandibular dental prosthesis 6.

The occlusion surfaces 12 of the prosthetic teeth 10 of the mandibular dental prosthesis 6 consist of an (easily) abradable material, i.e. of a material which is much more easily abradable than conventional customary materials for the construction of prosthetic teeth. This means that the abradable material is eroded at least twice as quickly as conventional customary materials for the construction of prosthetic teeth, preferably eroded at least ten times as quickly as conventional customary materials for the construction of prosthetic teeth.

The corresponding occlusion surfaces of the prosthetic teeth 8 of the maxillary dental prosthesis 4 preferably consist of a conventional customary material for the construction of prosthetic teeth, i.e. of a material that is more resistant to abrasion. Alternatively, however, the occlusion surfaces of the prosthetic teeth 8 of the maxillary dental prosthesis 4 also can consist of the same abradable material as the occlusion surfaces 12 of the prosthetic teeth 10 of the mandibular dental prosthesis 6. The thickness of the abradable material is preferably between 0.1 mm and 5 mm, wherein the thickness of the abradable material can be adapted to the abrasiveness of the corresponding material and/or can be adapted to the loading by the patient. By way of example, in the case of older individuals having a weak bite or in the case of known, for example inflammatory problems of the bearing surfaces or the tooth ridges, a more abradable material, i.e. a more easily or more quickly abradable material, can be selected. Alternatively, however, all of the prosthetic teeth 10 or all of the prosthetic teeth 8, 10 or also the entire mandibular dental prosthesis 2 and/or the entire maxillary dental prosthesis 1 can consist of the abradable material.

With use of the dental prostheses 1, 2, the occlusion surfaces 12 rub and grind against one another in some regions. In so doing, the abradable material of the occlusion surfaces 12 is abraded or removed or geometrically reduced in some regions over time. The resultant abraded regions are referred to as abrasion facets. The frequency and strength of the chewing movements determines in the long run (a few hours to a few weeks, depending on the abrasiveness of the material) the position, shape and depth of the abrasion facets and also the removed volumes of the abrasion facets. The abrasion facets are not uniformly distributed, since the prosthetic teeth 8, 10 do not contact one another at all occlusion surfaces 12 when the chewing movements are performed and also do not slide or rub over one another with equal frequency and at equal pressure and over equal lengths. Thus, the abrasion facets are characteristic for the chewing movements of the patient.

Due to the abradable material, which is easily removed, the abrasion facets are produced much more quickly than is usual and desired with final dental prostheses. After a period of use of a few hours of deliberate chewing movements up to a few weeks of normal use of the temporary dental prosthesis, the prosthesis can be removed.

In theory, the abrasiveness of the abradable material can also be selected such that the abrasion facets are produced after just a few chewing movements. To this end it can be useful for the patient to rinse out their mouth a few times so as to remove the eroded material from the oral cavity. The temporary dental prosthesis then replaces the height inspection using the known colored plates, in which case the dentist identifies the areas interfering the chewing movement on the basis of the coloring of the final prosthesis and can grind down said areas.

The abrasion facets are determined with the aid of a scanner in the oral cavity of the patient or preferably externally. The shape, position and/or depth of the abrasion facets is analyzed mathematically so as to determine or recalculate the typical chewing movements of the jaw of the patient. The original shape of the temporary dental prosthesis can be considered here mathematically by deducting the outer shape of the used temporary dental prosthesis from the outer shape of the new temporary dental prosthesis. In theory, it is sufficient to subtract only the outer shape of the coronal regions or only the outer shape of the occlusion surfaces of the prosthetic teeth from one another. To this end, unchanged fixed points should be discernible or defined. The outer shape of the new temporary dental prosthesis is in particular well known when this has been produced using a CAD-CAM method and therefore the CAD model of the outer surface of the temporary dental prosthesis is known and already stored. Temporary dental prostheses produced in this way or methods of this type are therefore preferred in accordance with the invention.

The chewing movements ascertained in this way can be used in order to produce a final dental prosthesis for the patient that matches the chewing movement.

The features of the invention disclosed in the above description and the claims, drawings and exemplary embodiments can be essential both individually and also in any combination for the implementation of the invention in the various embodiments thereof.

LIST OF REFERENCE SIGNS 1 maxillary dental prosthesis
2 mandibular dental prosthesis
4 maxillary prosthesis base
6 mandibular prosthesis base
8 maxillary prosthetic tooth
10 mandibular prosthetic tooth
12 occlusion surface

The invention claimed is:

1. A method for determining the chewing movement of a dentition from measured abrasion facets, the method comprising inserting a temporary dental prosthesis made of an abradable material in a patient, and after a maximum of 12 weeks of use of the temporary dental prosthesis, measuring the abrasion facets on the temporary dental prosthesis, and calculating the chewing movements of the dentition of the patient from the measured abrasion facets.

2. The method according to claim 1, comprising producing the temporary dental prosthesis by a rapid prototyping method or by an abrasive method.

3. The method according to claim 2, comprising determining a centric occlusion prior to producing the temporary dental prosthesis.

4. The method according to claim 1, comprising measuring the abrasion facets of the temporary dental prosthesis after said use using a scanner, determining a position, depth, and/or shape of the abrasion facets using a computer, and calculating the patient's chewing movements from data thus obtained relating to the abrasion facets.

5. The method according to claim 4, comprising measuring the abrasion facets of the temporary dental prosthesis after said use using a scanner, determining a position, depth, and/or shape of the abrasion facets using a computer by comparing a recording of the temporary dental prosthesis prior to said use, or of a CAD model of the temporary dental prosthesis prior to said use forming the basis for production of the temporary dental prosthesis, with the temporary dental prosthesis after said use.

6. A method for producing a final dental prosthesis including prosthetic teeth, comprising applying a method according to claim 1, calculating a position and an orientation of the prosthetic teeth of the final dental prosthesis on the basis of data relating to the patient's chewing movements ascertained using the temporary dental prosthesis, and producing the final dental prosthesis on the basis of this calculation.

7. A method according to claim 6, comprising producing the final dental prosthesis using a CAD-CAM method.

8. A method according to claim 1, wherein the temporary dental prosthesis has least one prosthetic tooth, wherein at least an occlusion surface of the at least one prosthetic tooth is made of a material that is abradable such that, within a maximum of 12 weeks of use as a temporary dental prosthesis by a patient, abrasion facets are produced on the at least one prosthetic tooth and are suitable for ascertaining chewing movements of a jaw of the patient, wherein a material thickness of at least 0.1 mm is eroded on at least one of the abrasion facets produced within a maximum of 12 weeks.

9. A method according to claim 1 comprising, after a maximum of 4 weeks of use of the temporary dental prosthesis, measuring the abrasion facets on the temporary dental prosthesis and calculating the chewing movements of the dentition of the patient from the measured abrasion facets.

* * * * *